United States Patent [19]
Santos

[11] Patent Number: 4,881,529
[45] Date of Patent: Nov. 21, 1989

[54] NECK SUPPORT COLLAR

[76] Inventor: Richard Santos, 21 Bird St., Apt. 1, Foxboro, Mass. 02035

[21] Appl. No.: 230,365

[22] Filed: Aug. 10, 1988

[51] Int. Cl.⁴ .......................... A61F 5/01; A61F 5/04; A61H 1/02
[52] U.S. Cl. ............................................ 128/75; 2/2; 2/415; 128/DIG. 23
[58] Field of Search .................... 128/75, 78, DIG. 23; 2/2, 22, 24, 411, 413, 414, 415

[56] References Cited

U.S. PATENT DOCUMENTS

| | | | |
|---|---|---|---|
| 2,657,385 | 11/1953 | Cushman et al. | 2/24 |
| 3,060,930 | 10/1962 | Grassl | 128/75 |
| 3,964,474 | 6/1976 | Fox | 128/87 B |
| 3,965,486 | 6/1976 | Lightbody | 2/24 |
| 4,099,523 | 7/1978 | Lourey | 128/75 |
| 4,142,252 | 3/1979 | Storer | 2/24 |
| 4,219,892 | 9/1980 | Rigdon | 2/24 |
| 4,232,663 | 11/1980 | Newton | 128/75 |

FOREIGN PATENT DOCUMENTS

| | | | |
|---|---|---|---|
| 2823370 | 12/1979 | Fed. Rep. of Germany | 2/413 |
| 568033 | 10/1975 | Switzerland | 2/413 |

*Primary Examiner*—Edgar S. Burr
*Assistant Examiner*—Moshe I. Cohen
*Attorney, Agent, or Firm*—Jerry T. Kearns

[57] ABSTRACT

A neck support collar for use by football players has a central section formed by a plurality of flexible plastic parallel adjacent tubes. A first group of the tubes has a diameter of one inch with a central longitudinal bore of one fourth inch diameter. A second group of the tubes has a diameter of one half inch and a central longitudinal bore of one eighth inch diameter. An end pad formed from soft perforated leather is attached to a first end of the central section and a support pad is attached to a second opposite end. The support pad has an interior rubber pad enclosed within a perforated leather covering. The support pad is subdivided into a plurality of adjacent sections which extend transversely to the tubes of the central section. A combination of buckle-strap and VELCRO fasteners are utilized to secure the collar around the neck of an individual. The device provides a constant balanced support at all sides of an individual's neck and serves to dampen shock created by impacts to the head of the individual.

12 Claims, 3 Drawing Sheets

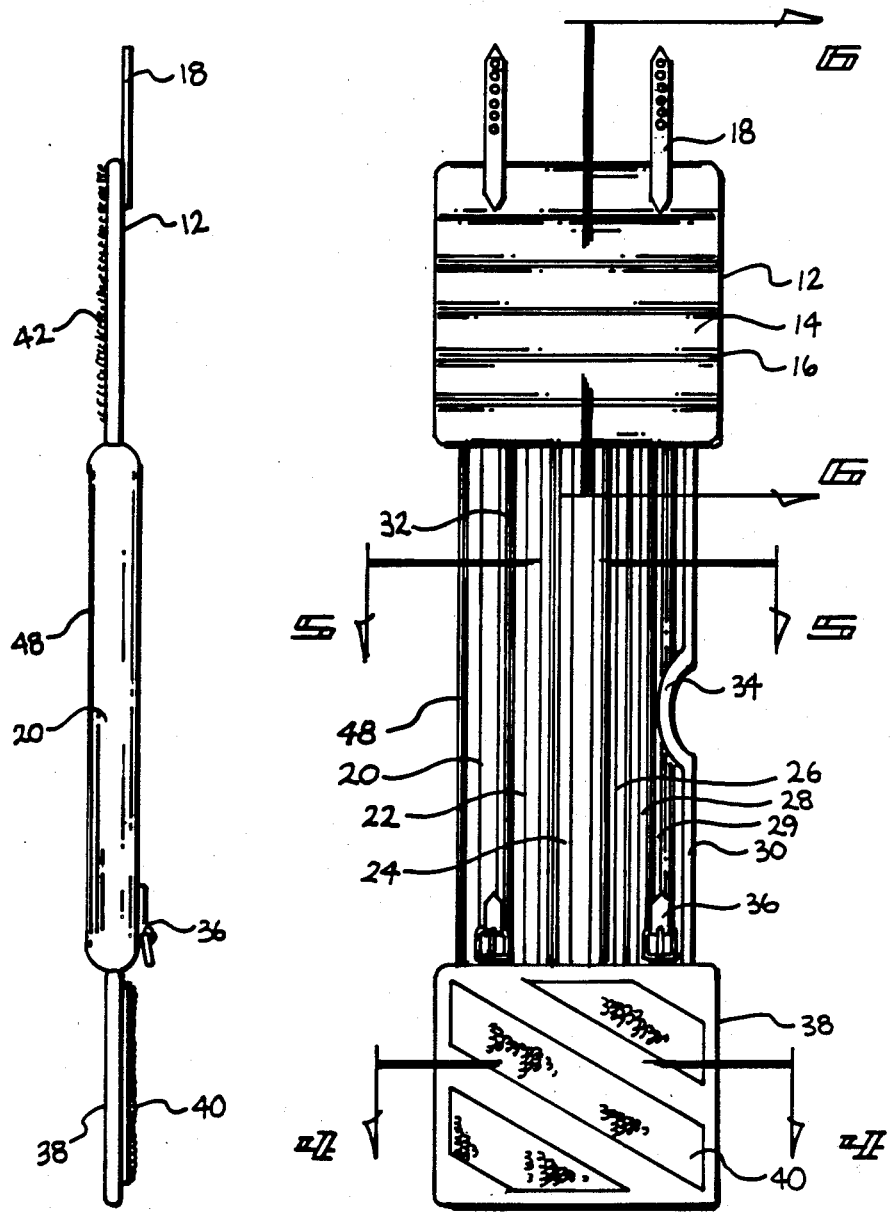

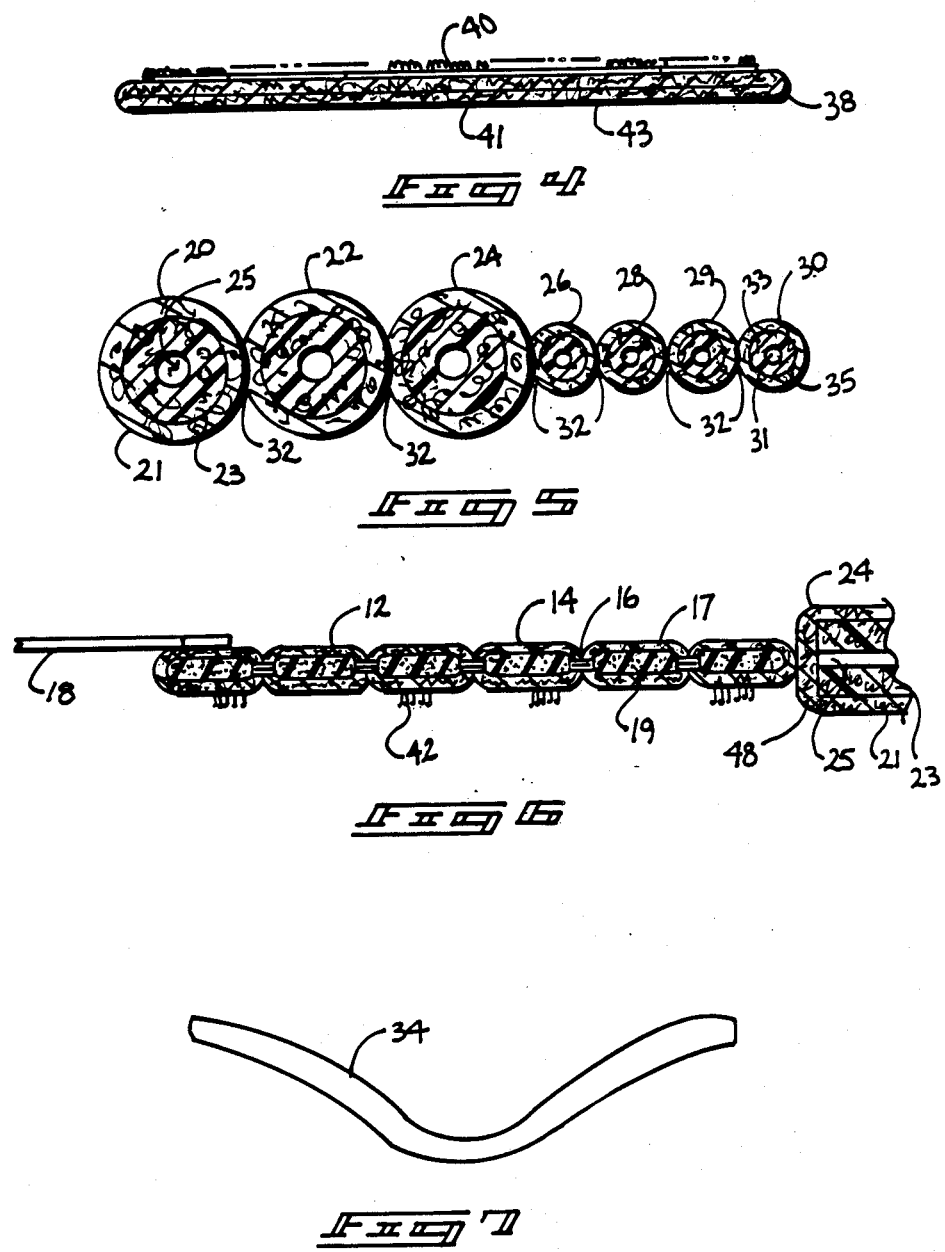

NECK SUPPORT COLLAR

BACKGROUND OF THE INVENTION

1. Field of the Invention

The present invention relates to neck support collars, and more particularly pertains to a new and improved neck support collar specifically adapted for use by football players. Football players are specially susceptible to crippling neck injuries. Specifically, fracture dislocations of the C5 and C6 vertebrae are extremely common. Such fracture dislocations frequently result in irreversible spinal cord injury. The problem has been aggravated by the use of extremely rigid protective helmets. While these helmets provide a large degree of protection against head injury, they frequently encourage individuals to utilize the helmet to deliver high impact blows. While the helmet protects the individual from head injury, the force of the blow is transmitted to the relatively unprotected neck vertebrae. In order to absorb and dissipate this impact force, the present invention provides an improved neck support collar.

2. Description of the Prior Art

Various types of neck support collars are known in the prior art. A typical example of such a neck support collar is to be found in U.S. Pat. No. 3,060,930, which issued to S. Grassl on Oct. 30, 1962. This patent discloses a neck support collar which includes a pair of elongated sponge rubber tubes covered by a flexible covering material. The collar has two interconnected sections for allowing adjustment of the width of the collar. The device utilizes cooperating buckle and strap fasteners for securement around the neck of an individual. As an alternative means of securement cooperating hook and loop fasteners such as VELCRO fasteners may be utilized. U.S. Pat. No. 3,964,474, which issued to J. Fox on June 22, 1976, discloses a neck support collar which is formed from plastic foam and includes a thin band of resilient plastic material biasing the foam into an annular shape. An outer covering of fabric material may be applied about the collar for purposes of cleanliness and enhancement of the appearance of the collar. U.S. Pat. No. 4,099,523, which issued to T. Lowrey on July 11, 1978, discloses a neck support collar for applying traction to the neck of a patient. The device includes a pair of relatively rigid hollow members telescopingly engaging each other. A bladder for the reception of air is disposed within the members. The bladder may be filled with fluid pressure in a controlled fashion to longitudinal separate the hollow members. The device provides a controlled amount of traction in an axial direction without a choking radial force component. U.S. Pat. No. 4,232,663, which issued to J. Newton on Nov. 11, 1980, discloses a neck support collar formed from a pad of resilient foam material with a scalloped depressed area at the middle of the inside surface of the collar for supporting the chin of an individual. Cooperating VELCRO fasteners are provided at opposite ends of the collar.

While the above mentioned devices are suited for their intended usage, none of these devices disclose a neck support collar which is formed from first and second groups of different diameter parallel adjacent flexible plastic tubes. Additionally, none of the aforesaid prior art neck support collars utilize a central section formed by a plurality of adjacent different diameter flexible plastic tubes in conjunction with an end support pad subdivided into a plurality of transversely extending support sections. Inasmuch as the art is relatively crowded with respect to these various types of neck support collars, it can be appreciated that there is a continuing need for and interest in improvements to such neck support collars, and in this respect, the present invention addresses this need and interest.

SUMMARY OF THE INVENTION

In view of the foregoing disadvantages inherent in the known types of neck support collars now present in the prior art, the present invention provides an improved neck support collar. As such, the general purpose of the present invention, which will be described subsequently in greater detail, is to provide a new and improved neck support collar which has all the advantages of the prior art neck support collars and none of the disadvantages.

To attain this, a representative embodiment of the concepts of the present invention is illustrated in the drawings and makes use of a central section formed by a plurality of flexible plastic parallel adjacent tubes. A first group of the tubes has a diameter of one inch with a central longitudinal bore of one-fourth inch diameter. A second group of the tubes has a diameter of one-half inch and a central longitudinal bore of one-eighth inch diameter. An end pad formed from soft perforated leather is attached to a first end of the central section and a support pad is attached to a second opposite end of the central section. The support pad has an interior rubber pad enclosed within a perforated leather covering. The support pad is subdivided into a plurality of adjacent sections which extend transversely to the tubes of the central section. A combination of buckle-strap and VELCRO fasteners are utilized to secure the collar around the neck of an individual. The device provides a constant balanced support at all sides of an individual's neck and serves to dampen shock created by impacts to the head of the individual.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of despcription and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, Which is measured by the claims, nor is it intended to be limiting as to the scope of the invention in any way.

It is therefore an object of the present invention to provide a new and improved neck support collar which has all the advantages of the prior art neck support collars and none of the disadvantages.

It is another object of the present invention to provide a new and improved neck support collar which may be easily and efficiently manufactured and marketed.

It is a further object of the present invention to provide a new and improved neck support collar which is of a durable and reliable construction.

An even further object of the present invention is to provide a new and improved neck support collar which is susceptible of a low cost of manufacture with regard to both materials and labor, and which accordingly is then susceptible of low prices of sale to the consuming public, thereby making such neck support collars economically available to the buying public.

Still yet another object of the present invention is to provide a new and improved neck support collar which provides in the apparatuses and methods of the prior art some of the advantages thereof, while simultaneously overcoming some of the disadvantages normally associated therewith.

Still another object of the present invention is to provide a new and improved neck support collar for dissipating impact forces sustained by football players.

Yet another object of the present invention is to provide a new and improved neck support collar which utilizes a central section formed by two groups of different diameter parallel adjacent flexible plastic tubes.

Even still another object of the present invention is to provide a new and improved neck support collar which provides an equally balanced supporting force at all sides of an individual's neck.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a plan view of the neck support collar of the present invention.

FIG. 3 is a side view of the neck support collar of FIG. 2.

FIG. 4 is a transverse cross sectional view, taken along line 4—4 of FIG. 2, illustrating the construction of the end pad of the neck support collar of the present invention.

FIG. 5 is a transverse cross sectional view, taken along line 5—5 of FIG. 2, illustrating the construction of the central section of the neck support collar of the present invention.

FIG. 6 is a longitudinal cross sectional view, taken along line 6—6 of FIG. 2, illustrating the construction of the support pad of the neck support collar of the present invention.

FIG. 7 is a detail view illustrating the configuration of the jaw location recess formed in the side wall formed in a longitudinal side edge of the central section.

DESCRIPTION OF THE PREFERRED EMBODIMENT

Figure 1:
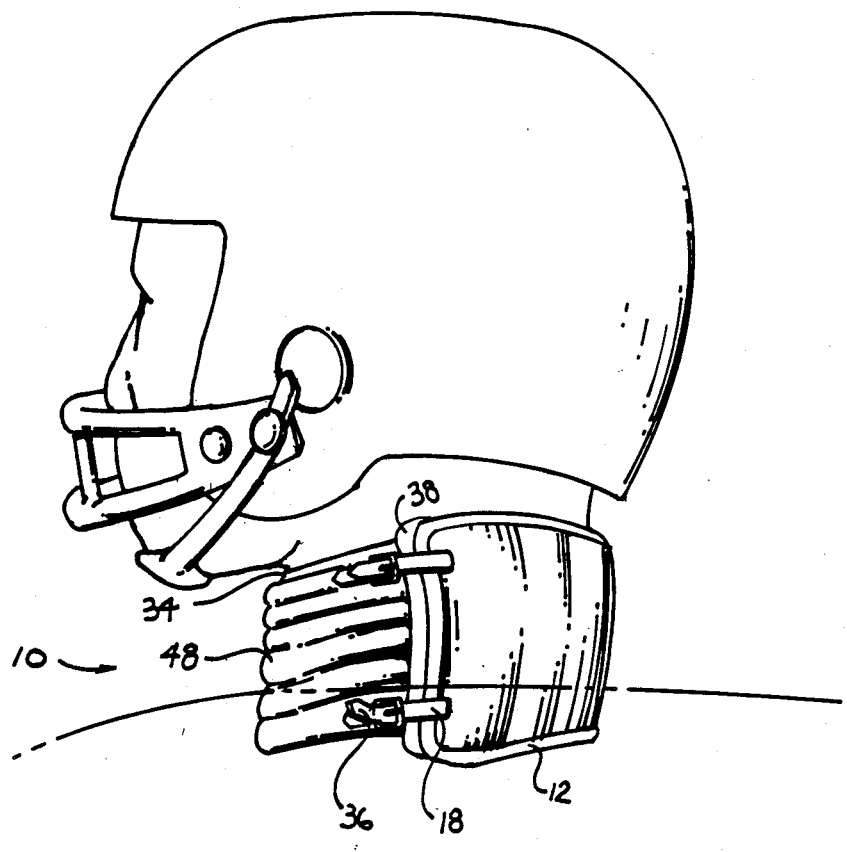
FIG. 1 is a side profile view of an individual football player wearing the neok support collar of the present invention.

With reference now to the drawings, and in particular to FIG. 1 thereof, a new and improved neck support collar embodying the principles and concepts of the present invention and generally designated by the reference numeral 10 will be described.

More specifically, it will be noted that the first embodiment 10 of the invention includes a support pad 12 which is secured in overlying relation over an end pad 38 and is additionally secured by cooperating buckle and strap fasteners 18 and 36 to a tubular central section 48. A jaw clearance recess 34 is formed in a top longitudinal side edge of the central section 48.

In FIG. 2, a plan view of the neck support collar 10 of the present invention is provided, in a stretched out condition removed from the individual's neck. The collar has a generally rectangular elongated central section 48 formed by a plurality of parallel adjacent tubes 20, 22, 24, 26, 28, 29 and 30. A first group of tubes 20, 22, and 24 is disposed adjacent a first longitudinal side edge of the central section 48, each having a diameter of one inch and a central longitudinal bore of one-fourth inch diameter. The second group of tubes 26, 28, 29 and 30, disposed adjacent a second longitudinal side edge of the central section 48, each have a diameter of one-half inch and a central longitudinal bore of one-eighth inch diameter. All of the tubes are formed from a flexible plastic material, and are provided with an outer tubular wrapping of a perforated leather material. A longitudinal seam 32 is sewn in the perforated leather covering between each pair of adjacent tubes. An arcuate jaw clearance recess 34 is formed at a midpoint in the second longitudinal side edge of the central section 48 and extends laterally through the outer tube 3 and partially through the next adjacent tube 29. The recess 34 is lined with a soft leather material. A pair of spaced buckle fasteners 36 are attached at a first end of the central section 48. A generally rectangular end pad 38 is sewn to the first end of the central section 48. The end pad 38 is formed from a soft perforated leather and is provided with a plurality of diagonally extending VELCRO fastening strips 40. A generally rectangular support pad 12 is attached to a second end of the central section 48, opposite the end pad 38. The support pad 12 has an interior rubber pad enclosed in a perforated leather covering. The support pad 12 is subdivided into a plurality of adjacent parallel sections 14 by a plurality of spaced sewn seams 16. The sections 14 extend transversely to the longitudinal axes of the tubes of the central section 48. A pair of fastening straps 18 extend from a free end of the support pad 12 for cooperation with the buckle fasteners 36.

As shown in FIG. 3, a back side of the support pad 12 is provided with VELCRO fastening strips 42 for cooperation with the VELCRO fastening strips 40 on the end pad 38.

In FIG. 4, a cross sectional view is provided which illustrates the construction of the end pad 38. The end pad 38 is formed from overlapping sewn leather material 41 which has a smooth back surface 43 and an upper surface provided with VELCRO fastening strips 40.

As shown in the cross sectional view of FIG. 5, the central section 48 is formed by seven adjacent tubes 20, 22, 24, 26, 28, 29 and 30. A first group of three larger diameter tubes 20, 22 and 24 each have a central flexible plastic tube 23 having a diameter of one inch and provided with a longitudinal extending bore 25 which has a diameter of one-fourth of an inch. Each of the tubes 20, 22 and 24 is provided with a tubular outer leather covering 21. Each of the tubes 26, 28, 29 and 30 of the second group of tubes has a central flexible plastic tube 33 having a diameter of one-half inch and provided with a central longitudinal bore having a diameter of one-eighth of an inch. Each of the tubes 26, 28, 29 and 30 is provided with a tubular leather covering 35. The leather coverings of each of the tubes is provided with a longitudinal extending seam 32 between each pair of adjacent tubes.

In FIG. 6, a cross sectional view is provided which illustrates the construction of the support pad 12. The support pad 12 has a sponge rubber interior pad enclosed by a perforated leather outer covering 17. A plurality of parallel spaced seams 16 subdivide the support pad 12 into a plurality of parallel sections 14, each having a width of about one inch. The support pad 12 is attached by sewing to the central tubular section 48.

FIG. 7 provides a detail view which illustrates the configuration of the leather lining of the jaw clearance recess 34 formed in the central tubular section 48, as illustrated in FIG. 2. The recess 34 is formed by a soft leather lining material. The recess 34 prevents the support collar from getting out of position during movement of the head of an individual from side to side.

The tubular construction of the central section 48, in conjunction with the transverse supporting sections 14 of the support pad 12, serve to provide balanced support for the neck of an individual in all directions. The shock wave from an impact is neutralized by transitory deformation of the flexible plastic tubes. The smaller diameter tubes allow the largest component of force to be transmitted for absorption adjacent the stronger lower portion of an individual's neck. The support collar of the present invention provides a sufficiently constant support to balance an individual's neck firmly from both sides and front to back, even when no neck muscle tension is exerted. The parallel side to side alignment of the flexible plastic tubes is essential in order to provide maximum impact absorption levels. The neck support will remain evenly balanced only if this correct alignment is observed. The resulting configuration serves to transmit impact forces away from the weakest C5 and C6 neck vertebrae.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A neck support collar, comprising:
   an elongated central section formed by two pluralities of parallel juxtaposed flexible plastic tubes, tubes of one plurality being of a different diameter than the tubes of the other plurality;
   an end pad attached to a first end of said central section;
   a support pad attached to a second end of said central section, opposite said first end; and
   means for releasably fastening said support pad to said end pad.

2. The neck support collar of claim 1, further comprising a flexible covering over said central section, said end pad and said support pad.

3. The neck support collar of claim 2, wherein said flexible covering comprises a perforated leather material.

4. The neck support collar of claim 1, wherein said plurality of tubes comprise a first group of larger diameter tubes and a second group of smaller diameter tubes.

5. The neck support collar of claim 4, wherein said first group of tubes have a diameter of one inch and said second group of tubes have a diameter of one-half inch.

6. The neck support collar of claim 5, further comprising a longitudinal bore extending through each of said tubes, said longitudinal bore having a diameter of one-fourth inch in said first group of tubes and a diameter of one-eighth inch in said second group of tubes.

7. The neck support collar of claim 1, wherein said support pad comprises:
   an interior rubber pad enclosed within a flexible covering; and
   said support pad subdivided into a plurality of parallel adjacent sections which extend transversely to said tubes.

8. The neck support collar of claim 7, wherein said support pad is subdivided by a plurality of spaced parallel seams.

9. The neck support collar of claim 1 wherein said releasable fastening means comprises cooperating hook and loop fastening strips on said end pad and said support pad.

10. The neck support collar of claim 9, further comprising cooperating buckle and strap fastening means on said support pad and on said first end of said central section.

11. The neck support collar of claim 1, further comprising an arcuate recess at a midpoint of one longitudinal side edge of said central section.

12. A neck support collar, comprising:
   a generally rectangular elongated central section formed by a plurality of parallel adjacent tubes;
   a first group of said plurality of tubes disposed adjacent a first longitudinal side edge of said central section, formed by three flexible plastic tubes, each having a diameter of one inch and a central longitudinal bore of one-fourth inch diameter;

a second group of said plurality of tubes disposed adjacent a second longitudinal side edge of said central section, formed by three flexible plastic tubes, each having a diameter of one half inch and a central longitudinal bore of one-eighth inch diameter;

each of said plurality of tubes having an outer tubular wrapping of a perforated leather material;

a longitudinal seam sewn in said leather material between each pair of adjacent tubes;

an arcuate recess formed at a midpoint in said second longitudinal side edge, said recess extending laterally through an outer one and partially through a next adjacent one of said second group of tubes;

said recess lined with a soft leather material;

a pair of spaced buckle fasteners at a first end of said central section;

a generally rectangular end pad attached to said first end of said central section;

said end pad formed from a soft perforated leather sewn to said central section, a first outer side of said end pad having a plurality of diagonally extending first hook and loop fastening strips;

a generally rectangular support pad attached to a second end of said central section, opposite said first end;

said support pad having an interior rubber pad enclosed within a leather covering;

said support pad having a plurality of parallel spaced seams which subdivide the support pad into a plurality of adjacent sections which extend transversely to said plurality of tubes;

a back side of said support pad provided with second hook and loop fastening strips for cooperation with said first hook and loop fastening strips; and a pair of fastening straps extending from a free end of said support pad for cooperation with said buckle fasteners.

* * * * *